United States Patent
Qu et al.

(10) Patent No.: US 11,307,187 B2
(45) Date of Patent: Apr. 19, 2022

(54) DETECTION OF AREA OF ABNORMAL AIR QUALITY WITHIN A GEOGRAPHICAL AREA

(71) Applicant: INTERNATIONAL BUSINESS MACHINES CORPORATION, Armonk, NY (US)

(72) Inventors: Junmei Qu, Beijing (CN); Lingyun Wang, Beijing (CN); Xin Xin Bai, Beijing (CN); Xi Xia, Beijing (CN); Jin Yan Shao, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 356 days.

(21) Appl. No.: 16/589,714

(22) Filed: Oct. 1, 2019

(65) Prior Publication Data

US 2021/0096119 A1    Apr. 1, 2021

(51) Int. Cl.
*G01N 33/00*     (2006.01)
*G08C 25/04*     (2006.01)
*G01W 1/02*      (2006.01)
*H04W 4/38*      (2018.01)
(Continued)

(52) U.S. Cl.
CPC .......... *G01N 33/0075* (2013.01); *G01W 1/02* (2013.01); *G08B 21/12* (2013.01); *G08C 25/04* (2013.01);
(Continued)

(58) Field of Classification Search
CPC .... G01D 9/005; G01N 33/0075; G01N 35/00; G01N 3/04; G01W 1/00; G01W 1/02;
(Continued)

(56) References Cited

U.S. PATENT DOCUMENTS

2016/0125307 A1 * 5/2016 Zheng .................... G06N 20/00
                                                              706/12
2016/0370339 A1 * 12/2016 Liu ...................... G01N 33/0075
(Continued)

FOREIGN PATENT DOCUMENTS

EP    3622625 A2    11/1994
WO    32063539 A1   8/2002

OTHER PUBLICATIONS

Xu, Wenxuan et al., "Understanding the Spatial-Temporal Patterns and Influential Factors on Air Quality Index: The Case of North China", Published in: International Journal of Environmental Research and Public Health, Print Date: Aug. 1, 2019 (Year: 2019).*
(Continued)

*Primary Examiner* — Stephen R Burgdorf
(74) *Attorney, Agent, or Firm* — Scott Dobson

(57) ABSTRACT

An abnormal area is detected using an initial spatial weights matrix between pairs of air quality sensors in a plurality of air quality sensors distributed across a geographical area and air quality data for each air quality sensor. The spatial weights matrix utilizes a distance between pairs of air quality sensors and wind direction through the geographical area. The initial spatial weights matrix and air quality data are used to calculate a plurality of local moran's indexes, one for each air quality sensor. The plurality of local moran's indexes are used to divide the plurality of air quality sensors into four groups. The groups are classified as proper or improper, and the proper groups are identified as abnormal areas.

19 Claims, 7 Drawing Sheets

(51) Int. Cl.
  *H04W 4/021* (2018.01)
  *G08B 21/12* (2006.01)
  *H04Q 9/00* (2006.01)

(52) U.S. Cl.
  CPC .............. *H04Q 9/00* (2013.01); *H04W 4/021* (2013.01); *H04W 4/38* (2018.02); *H04Q 2209/40* (2013.01)

(58) Field of Classification Search
  CPC . G05B 13/0255; G05B 28/0283; G06F 17/17; G06F 30/28; G06K 9/527; G06N 20/00; G08B 13/19613; G08B 21/12; G08C 25/04; H04L 67/12; H04L 67/18; H04Q 9/00; H04Q 2209/40; H04W 4/021; H04W 4/38
  USPC ........................................................ 73/31.02
  See application file for complete search history.

(56) References Cited

U.S. PATENT DOCUMENTS

| | | |
|---|---|---|
| 2018/0247526 A1 | 8/2018 | Pariseau |
| 2019/0033281 A1 | 1/2019 | Mou et al. |
| 2019/0113445 A1 | 4/2019 | Zhang et al. |

OTHER PUBLICATIONS

Cao, Qilong et al., "China's Air Quality and Respiratory Disease Mortality Based on the Spatial Panel Model". Published in: International Journal of Environmental Research and Public Health, Print Date: 1-Sep. 2017 (Year: 2017).*

Zou et al., "Spatial Cluster Detection of Air Pollution Exposure Inequities across the United States," Plos One, Mar. 19, 2014, https://doi.org/10.1371/journal.pone.0091917.

* cited by examiner

DETECTION OF AREA OF ABNORMAL AIR QUALITY WITHIN A GEOGRAPHICAL AREA

FIELD OF THE INVENTION

The present invention relates to air quality monitoring.

BACKGROUND OF THE INVENTION

Accurate monitoring or air quality is used to identify areas of abnormal air quality. These areas are then supervised, for example, to identify causes of the abnormal air quality, to implement measures to improve air quality and to provide air quality alerts as needed. Traditional sensors for monitoring air quality were large sensors that provided accurate measurements of air pollutants, for example, particulate matter, sulfur dioxide, carbon monoxide, nitrogen dioxide, and ozone. To cover large geographical areas, multiple sensors are required. However, the traditional large sensors were expensive, making the deployment of multiple sensors cost prohibitive.

To reduce costs while monitoring large geographical areas, lower cost monitors such as smart air quality sensors are deployed in many locations across the large geographical areas. While the data quality associated with the lower cost monitors is less than the large sensors, these lower costs monitors can detect air quality data trends, and the air quality data are consistent among the lower cost monitors. Therefore, detection of abnormal air quality utilized comparisons between air quality data from a single air quality monitor and an average value of air quality data obtained from multiple air quality monitors surrounding the single air quality monitor.

Conventional methods for detecting abnormal air quality using air quality data from the air quality monitors identified abnormalities at single air quality monitors and boundaries or lines between adjacent areas having different air quality levels. A need still exists for identifying an area of abnormal air quality data and for adjusting a size of the area of abnormal air quality data to achieve an area that can be supervised in a reasonable period of time.

SUMMARY OF THE INVENTION

Exemplary embodiments are directed to systems and methods that detect areas of abnormal air quality using air quality data from a plurality of air quality monitors and that dynamically adapt the grouping of air quality monitors to achieve areas of abnormal air quality having a reasonable size.

Exemplary embodiments are directed to a method for identifying an abnormal area. An initial spatial weights matrix is identified between pairs of air quality sensors in a plurality of air quality sensors distributed across a geographical area. The spatial weights matrix utilizes a distance between pairs of air quality sensors and wind direction through the geographical area. Air quality data are obtained from each air quality sensor, and the initial spatial weights matrix and air quality data are used to calculate a plurality of local moran's indexes, one for each air quality sensor. The plurality of local moran's indexes is used to divide the plurality of air quality sensors into four groups.

Exemplary embodiments are directed to computer-readable medium containing a computer-readable code that when read by a computer causes the computer to perform a method for identifying an abnormal area. An initial spatial weights matrix is identified between pairs of air quality sensors in a plurality of air quality sensors distributed across a geographical area. The spatial weights matrix utilizes a distance between pairs of air quality sensors and wind direction through the geographical area. Air quality data are obtained from each air quality sensor, and the initial spatial weights matrix and air quality data are used to calculate a plurality of local moran's indexes, one for each air quality sensor. The plurality of local moran's indexes is used to divide the plurality of air quality sensors into four groups.

Exemplary embodiments are directed to system for identifying an abnormal area. The system includes a plurality of air quality sensors distributed across a geographical area and a data collection system in communication with the plurality of air quality sensors to obtain air quality data from each air quality sensor and wind direction data through the geographical area. A clustering module in communication with the data collection system is used to identify an initial spatial weights matrix between pairs of air quality sensors using a distance between pairs of air quality sensors and wind direction, to calculate a plurality of local moran's indexes, one for each air quality sensor, from the initial spatial weights matrix and air quality data and to divide the plurality of air quality sensors into four groups based on the plurality of local moran's indexes.

DETAILED DESCRIPTION

Exemplary embodiments are directed to systems and methods for identifying one or more areas of abnormal air quality readings, i.e., abnormal areas, across or within a given geographical area. The air quality sensors in a plurality of air quality sensors are distributed across the geographical area, and the abnormal areas are portions of the overall geographical area containing clusters or groupings of air quality sensors reporting air quality data that differ from, i.e., are abnormal relative to, the air quality data from adjacent or surrounding sensors. These clusters or groups of air quality sensors and the abnormal areas containing the groups of air quality sensors are then classified as proper groups or improper groups. This classification is made by comparing each identified group of air quality sensors and the associated abnormal area against historical data for previously classified proper and improper groups, e.g., proper in size and proper in the relative values of the air quality sensors. Proper groups are outputted or communicated to the appropriate individuals or organizations for supervision and possible remediation or other actions to protect public and environmental health. Improper groups are further divided into sub-groups and classified using the same steps and mechanisms employed to identify the types of clusters at each air quality sensor and to place the air quality sensors into groups. After dividing the improper groups, proper sub-groups are output for supervision and improper sub-groups are further divided. Clustering and classification are repeated iteratively until all identified abnormal areas, groups and sub-groups are proper.

Figure 1:
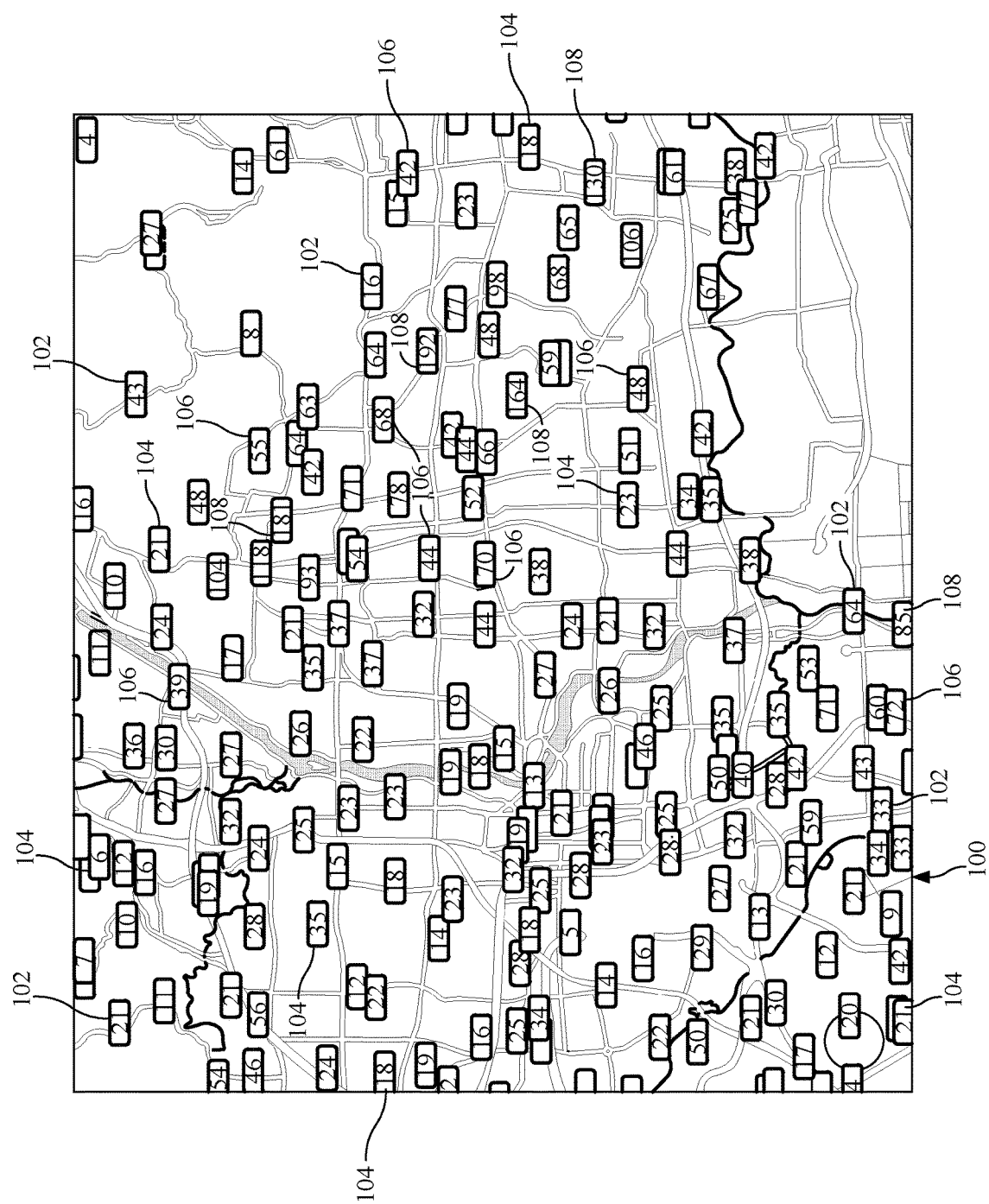
FIG. 1 is a representation of a geographical area containing a plurality of air quality monitors.

Referring initially to FIG. 1, exemplary embodiments utilize a plurality of air quality sensors 102 distributed across a geographical area 100. Each air quality sensor has an associated set of location coordinates. Suitable location coordinates include spherical coordinates, e.g., latitude and longitude, two-dimensional coordinates and three-dimensional coordinates. The air quality sensors can all be the same type of air quality sensors or can be two or more different types of air quality sensors. In one embodiment, the air quality sensors are smart air quality sensors that utilize telemetry to measure and detect elevated levels of air pollutants to relay those measurements to a data collection system using, for example, WIFI, Bluetooth or cellular based networks. The air quality sensors are capable of generating consistent quality data, i.e., consistent over time for a given air quality sensor and consistent across all air quality sensors.

The air quality sensors measure, for example, the level of particulates in the air and the concentration of different chemical species in the air, and generate air quality data. Suitable pollutant measurements include, but are not limited to, particulate matter, sulfur dioxide, carbon monoxide, nitrogen dioxide, and ozone. In one embodiment, the air quality data are used directly in making clustering and classification determinations. Alternatively, the air quality data are converted into an overall air quality index for each air quality sensor. The resulting air quality indexes are used in making clustering and classification determinations. In one embodiment, the air quality indexes are generated at each air quality sensor. Alternatively, the air quality data are communicated to a data collection system that computes the air quality index for each air quality sensor.

At any given time, each air quality sensor generates air quality data, e.g., individual air quality data or an air quality index. At a given point in time, the plurality of air quality sensors in the geographical area include relatively low pollutant level air quality sensors 104, relatively high pollutant level air quality sensors 106 and anomalous air quality sensors 108. The anomalous air quality sensors have associated air quality data deviating substantially, i.e., higher or lower, from adjacent air quality sensors. Exemplary embodiments identify groupings of air quality sensors occupying given portions of the geographical area based on the value of given air quality sensors relative to the other air quality sensors. These groupings are compared with historical data on groupings to ensure that they can be reasonably supervised for purposes of improving air quality and monitoring potential public health risks.

Figure 2:
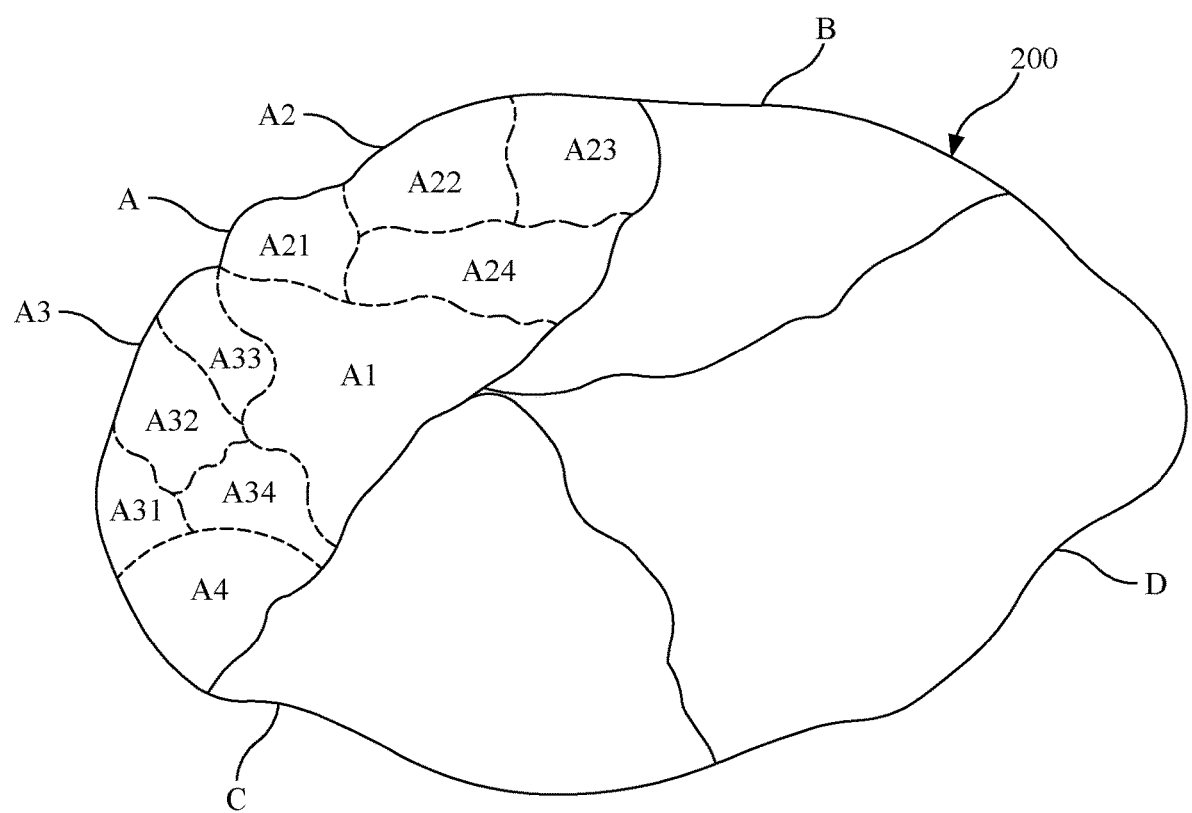
FIG. 2 is a schematic representation of iteratively defining groups and sub-groups.

Referring now to FIG. 2, exemplary embodiments group the air quality sensors in a given geographical area 200 into four groups using the air quality data obtained from each air quality sensor. These four groups are illustrating as defining four areas (A,B,C,D) that each contain the air quality sensors associated with one of the groups. While four groups are illustrated, a given geographic area or a given portion of the geographical area can be divided into more than four groups or four areas or less than four groups or four areas. The resulting four groups and four areas are classified as either proper groups or improper groups. As illustrated, groups B, C and D are proper groups, i.e., abnormal areas. Therefore, these groups are output to an appropriate authority, and the area and air quality sensors for those groups are designated for supervision. Group A is an improper group. Therefore, the groups in those areas are subdivided into four sub-groups (A1, A2, A3, A4). Sub-groups A1 and A4 are proper and are output for supervision. Sub-groups A2 and A3 are improper and are further divided into four sub-sub-groups each (A21, A22, A23, A24 and A31, A32, A33, A34). All eight sub-sub-groups are proper. Grouping and classifying are stopped, and the sub-sub-groups are output and designated for supervision.

For purposes of illustration, each group, sub-group, and sub-sub-group is illustrated as a separate area. However, one or more of the areas can cross or overlap, as the air quality sensors associated with a first type of clustering may be intermingled or interspersed with air quality sensors associated with a second type of clustering. Therefore, any given group can include air quality sensors distributed across a rather large portion of the geographical area. Large areas cannot be supervised in a reasonable period of time. Therefore, the size of each area containing the sensors in a given group of sensors, among other factors, is considered in determining whether a given group is proper. The groups are subdivided until the area occupied by each group is a reasonable area.

Figure 3:
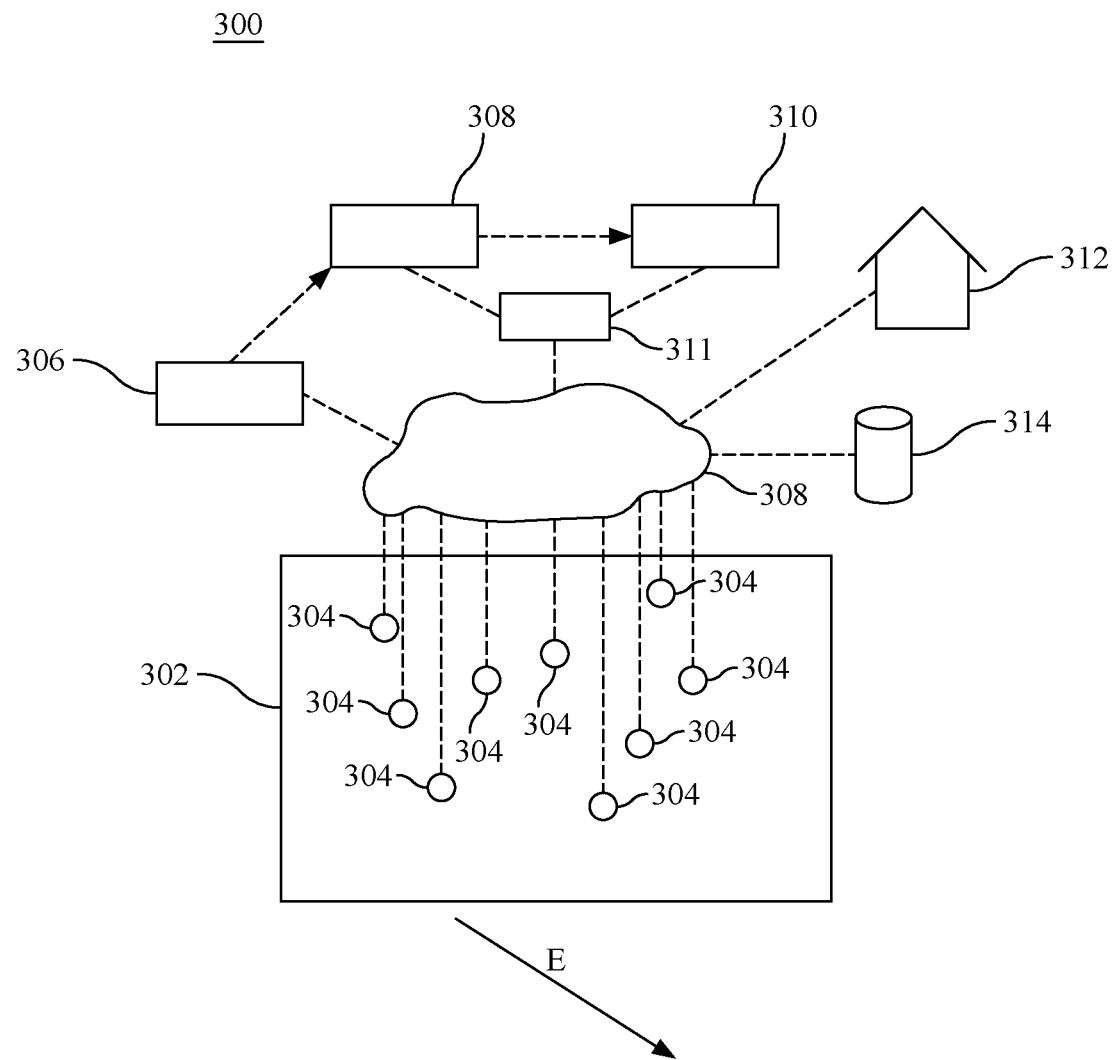
FIG. 3 is a schematic representation of a system for detecting an abnormal area.

Referring to FIG. 3, a system 300 for identifying one or more abnormal areas is illustrated. The system includes a plurality of air quality sensors 304 distributed across a geographical area. The total number of air quality sensors can be dozens, hundreds or thousands of air quality sensors. In one embodiment, the sensors are not evenly distributed across the geographical area and may be concentrated in one or more regions of the geographical area. Each air quality sensor has an associated location coordinate. Suitable location coordinates include longitude and latitude data, two-dimensional coordinates and three-dimensional coordinates.

The system includes a data collection module 306 in communication with each one of the plurality of air quality sensors. The data collection module is in communication with the air quality sensors across one or more wide area or local area networks 308. These networks include WIFI, Bluetooth and cellular based networks. The data collection module obtains air quality data from each air quality sensor. In addition, the data collection module obtains data on wind direction E through or across the geographical area.

Figure 4:
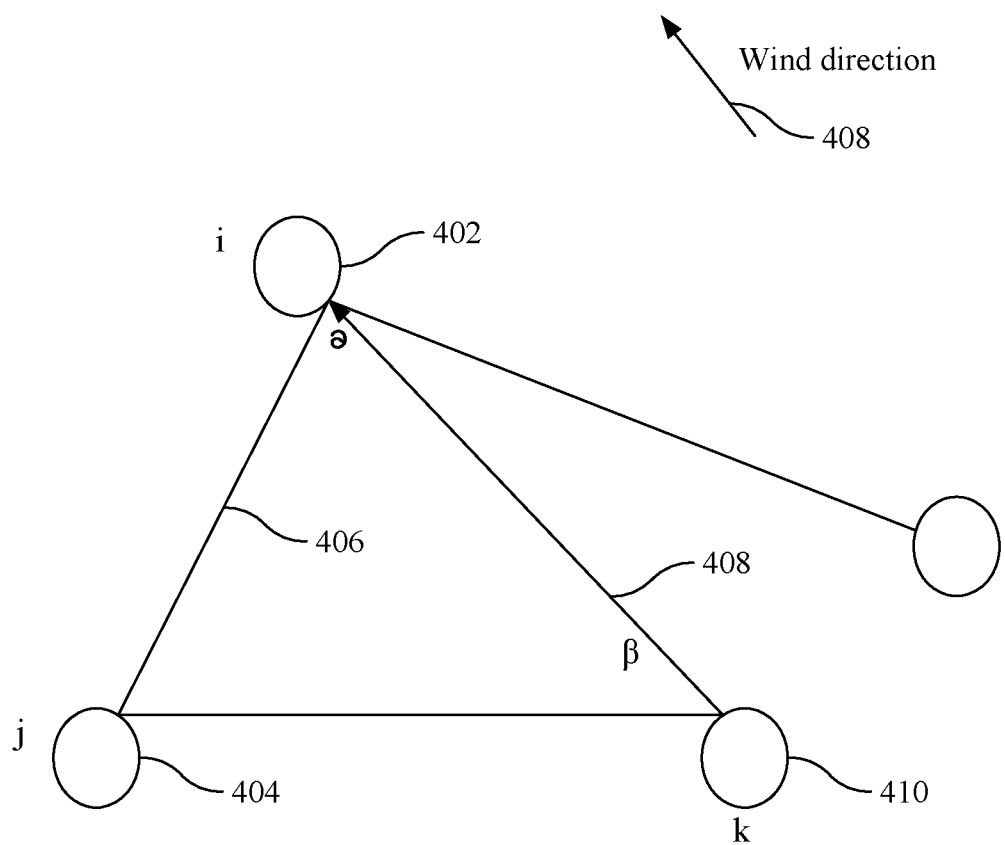
FIG. 4 is a schematic representation of wind direction and vectors between nodes for determining spatial weights.

The system includes a clustering module in communication with the data collection system. The clustering module provides the functionality to cluster the air quality sensors into the plurality of groups. The clustering module identifies an initial spatial weights matrix, $w_{i,j}$, between pairs of air quality sensors. The clustering module uses the distance, Dis(i,j), between pairs of air quality sensors (i,j) and wind direction in determining the initial spatial weights matrix. Referring to FIG. 4, the clustering module calculates the distance between a pair of air quality sensors containing a first air quality sensor 402, $i$, and a second air quality sensor 404, $j$, using the location coordinates associated with each air quality sensor. The clustering module also determines a node vector between pairs of air quality sensors. The node vector extends along the distance between the two air quality sensors and has an associated direction, either from the first air quality sensor to the second air quality sensor or from the second air quality sensor to the first air quality sensor. The clustering module also obtains the wind direction 408. In one embodiment, the wind direction is in degrees.

The clustering module sets the spatial weight between the given pair of air quality sensors based on a comparison between the wind direction and the node vector associated with the pair of air quality sensors. The spatial weight between the pair of air quality sensors is set as a cosine of an angle between the wind direction and the node vector divided by the distance between the given pair of air quality sensors, w(i, j)=1/Dis(i, j)*cos, when the given pair of air quality sensors has at least a node vector component extending in the wind direction, i.e., when the wind direction, at least in part, extends from one air quality sensor to the other air quality sensor along the node vector. Conversely, the spatial weight between the pair of air quality sensors is set as the negative of the cosine of the angle between the wind direction and the node vector divided by the distance between the given pair of air quality sensors, w(i, j)=−1/Dis (i, j)*cos, when the given pair of air quality sensors lack at least a node vector component extending in the wind direction.

As illustrated in FIG. 4, the wind direction 408 parallels a vector between the first air quality sensor 402 and a third air quality sensor 410, k. For a vector extending from the second air quality sensor to the first air quality sensor, the angle between that vector and the wind direction is ∂, and the spatial weight is $$w_{i,j} = \frac{\cos\partial}{Dis_{i,j}}.$$

For a vector extending from the third air quality sensor to the first air quality sensor, the spatial weight is $$w_{i,k} = \frac{1}{Dis_{i,k}}.$$

For a vector extending from the second air quality sensor to the third air quality sensor, the angle between that vector and the wind direction is β, and the spatial weight is $$w_{j,k} = -\frac{\cos\beta}{Dis_{j,k}},$$

and for a vector extending from the third air quality sensor to the second air quality sensor, the spatial weight is $$w_{k,j} = \frac{\cos\beta}{Dis_{j,k}}.$$

Having identified the initial spatial matrix, the clustering module calculates a plurality of local moran's indexes, one for each air quality sensor using the initial spatial weights matrix and air quality data. The local moran's index is given by $$I_i = \frac{x_i - \overline{X}}{S_i^2} \sum_{j=1, j \neq i}^{n} w_{i,j}(x_j - \overline{X}),$$

where $x_i$ is the value of a given air quality sensor, $\overline{X}$ is the mean value of all air quality sensors, $x_j$ is the value of the $j^{th}$ air quality sensor, n is the total number of air quality sensors and the sample variance is $$S_i^2 = \frac{\sum_{j=1, j \neq i}^{n}(x_j - \overline{X})^2}{n - 1}.$$

The local moran's index identifies four types of clustering around a given air quality sensor, a statistically significant cluster of high air quality values (H,H), a statistically significant cluster of low air quality values (L,L), a high value outlier comprising a high air quality value surrounded by low air quality values (H,L), and a low value outlier comprising a low air quality value surrounded by high air quality values (L,H). The value of I for each air quality sensor determines the associated clustering, and the clustering module uses the value of I to divide the plurality of air quality sensors into four groups.

Returning to FIG. 3, the system includes a classification module 310 in communication with the clustering module to classify each one of the four groups as either a proper group or an improper group using a supervised classification model. The classification module builds the supervised classification model by obtaining data on a plurality previously defined groups of air quality sensors. The data include the location of each air quality sensor in the group, the air quality value at each air quality sensor and a classification label, i.e., proper or improper. Features of the air quality data in each group are used as inputs for the model and the classification label as an output for the model. The features include a largest inner group air quality data difference, a median inner group air quality difference, a largest whole group air quality data difference, and a geographical size associated with each group. The desired type of model is chosen, and the classification module uses historical data from each previously defined group to train the supervised classification model. Suitable types of models include, but are not limited to, neural network, decision tree and logic regression. The classification module then inputs the features of each newly defined group into the trained supervised classification model, which outputs either proper or improper. Therefore, each newly defined group has features that are consistent with previously defined proper groups.

The system includes an output module 311 in communication with the classification module and the clustering module to output each group classified as a proper group for supervision as an abnormal area. The abnormal areas are output to one or more organizations 312 that perform the supervision. The output module also designates each group classified as an improper group for further subdivision. The clustering module subdivides each group classified as an improper group. The clustering module uses the spatial weights matrix and calculates the local moran's index for each air quality sensor to divide each improper group into four sub-groups. The new sub-groups are communicated to the classification module, and each one of the four sub-groups from each improper group is classified as either a proper sub-group or an improper sub-group using the supervised classification model. The system is used to repeat this process until all groups and sub-groups are classified as proper and are output to an organization for supervision of each abnormal area.

In one embodiment, the system includes a database 314. The database is in communication with all modules and components of the system. The database stores, for example, current and historical air quality data, a history of previously defined groups, the initial spatial matrix and moran's indexes. In one embodiment, the database also stores the software that provides the functionality to all modules in the system. Each module includes both the software and hardware, e.g., processor and communications, sufficient to provide the desired functionality in the module. The modules can be arranged as a distributed computing system or a cloud-based computing system.

Figure 5:
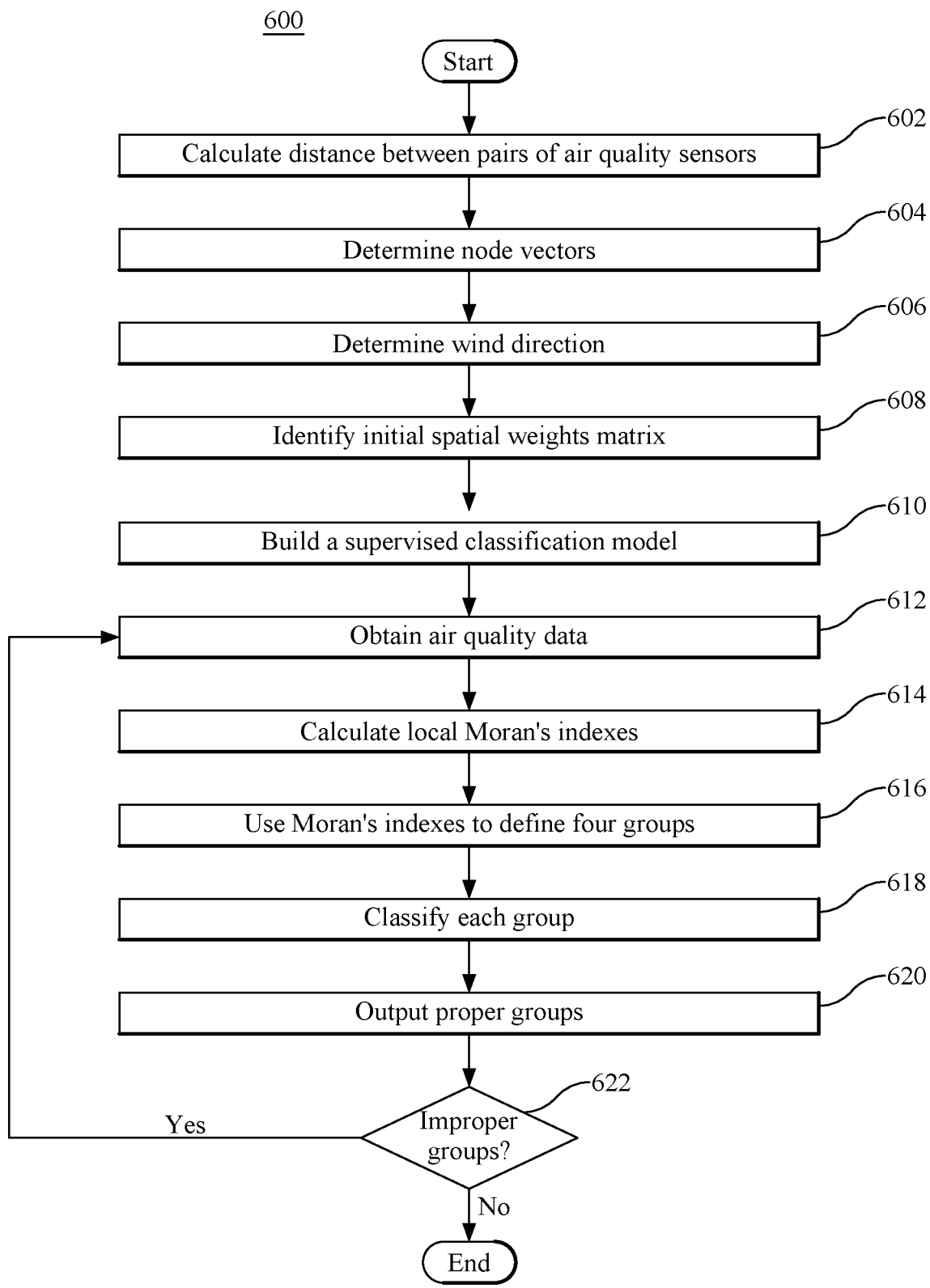
FIG. 5 is a flow chart illustrating an embodiment of a method for detecting an abnormal area.

Referring now to FIG. 5, exemplary embodiments are directed to a method for identifying an abnormal area 600 or for identifying multiple abnormal areas in a given geographical area. Distances between pairs of air quality sensors are calculated 602 using location coordinates associated with each air quality sensor. A node vector between pairs of air quality sensors is determined 604, and the wind direction is determined 606. An initial spatial weights matrix between pairs of air quality sensors in a plurality of air quality sensors distributed across a geographical area is identified 608. The spatial weights matrix utilizes a distance between pairs of air quality sensors and wind direction through the geographical area.

In defining the initial spatial weights matrix, a spatial weight between each given pair of air quality sensors is defined based on a comparison between the wind direction and the node vector associated with the given pair. In one embodiment, the spatial weight between the given pair of air quality sensors is defined as a cosine of an angle between the wind direction and the node vector divided by the distance between the given pair of air quality sensors when the given pair of air quality sensors has at least a node vector component extending in the wind direction. In addition, the spatial weight between the given pair of air quality sensors is defined as the negative of the cosine of the angle between the wind direction and the node vector divided by the distance between the given pair of air quality sensors when the given pair of air quality sensors lack at least a node vector component extending in the wind direction.

A supervised classification model is built 610. In one embodiment, a plurality previously defined groups of air quality sensors are obtained. Each previously defined group includes node locations for the air quality sensors in the group, air quality data obtained from the air quality sensors in the group and a classification label for the entire group. The classification label is either proper or improper. A supervised classification model is defined with features of the group and the air quality sensors in the group as model inputs and the classification label as a model output. In one embodiment, the features include, a largest inner group air quality data difference, a median inner group air quality difference, a largest whole group air quality data difference, and a geographical size. The previously defined groups are used to train the supervised classification model.

Air quality data are obtained from each air quality sensor 612. A plurality of local moran's indexes are calculated 614 using the initial spatial weights matrix and air quality data. One local moran's index is calculated for each air quality sensor. The plurality of local moran's indexes are used to divide the plurality of air quality sensors into four groups 616. The four groups are a statistically significant cluster of high air quality values, a statistically significant cluster of low air quality values, a high value outlier comprising a high air quality value surrounded by low air quality values, and a low value outlier comprising a low air quality value surrounded by high air quality values.

Each one of the four groups is classified as either a proper group or an improper group 618. In one embodiment, each one of the four groups is classified using the supervised classification model. Each group classified as a proper group is output for supervision 620 as an abnormal area. A determination is made regarding whether any of the groups is classified as an improper group. If improper groups are identified, the improper groups are subdivided using the same original spatial weights matrix and steps used to create the original groups. Therefore, air quality data are obtained from each air quality sensor in each improper group 612, and the initial spatial weights matrix and air quality data are used to calculate a plurality of local moran's indexes 614, one for each air quality sensor in each improper group. The plurality of local moran's indexes is used to divide the plurality of air quality sensors in each improper group into four sub-groups 616, and each one of the four sub-groups from each improper group is classified as either a proper sub-group or an improper sub-group using the supervised classification model. Subdividing, grouping and classification continue until no improper groups are classified and all proper groups have been output for supervision.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that although a detailed description on cloud computing is provided, implementation of the teachings provided herein are not limited to a cloud computing environment. Rather, embodiments of the present invention are capable of being implemented in conjunction with any other type of computing environment now known or later developed. Cloud computing is a model of service delivery for enabling convenient, on-demand network access to a shared pool of configurable computing resources, e.g., networks, network bandwidth, servers, processing, memory, storage, applications, virtual machines, and services, that can be rapidly provisioned and released with minimal management effort or interaction with a provider of the service.

This cloud model may include at least five characteristics, at least three service models, and at least four deployment models. The five characteristics are on-demand self-service, broad network access, resource pooling, rapid elasticity and measured service. Regarding on-demand self-service, a cloud consumer can unilaterally provision computing capabilities, such as server time and network storage, as needed automatically without requiring human interaction with the service's provider. Broad network access refers to capabilities that are available over a network and accessed through standard mechanisms that promote use by heterogeneous thin or thick client platforms, e.g., mobile phones, laptops, and PDAs. For resource pooling, the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction, e.g., country, state, or datacenter. Rapid elasticity refers to capabilities that can be rapidly and elastically provisioned, in some cases automatically, to quickly scale out and rapidly released to quickly scale in. To the consumer, the capabilities available for provisioning often appear to be unlimited and can be purchased in any quantity at any time. For measured service, cloud systems automatically control and optimize resource use by leveraging a metering capability at some level of abstraction appropriate to the type of service, e.g., storage, processing, bandwidth, and active user accounts. Resource usage can be monitored, controlled, and reported, providing transparency for both the provider and consumer of the utilized service.

The three service models are Software as a Service (SaaS), Platform as a Service (PaaS) and Infrastructure as a Service (IaaS). Software as a service provides the capability to the consumer to use the provider's applications running on a cloud infrastructure. The applications are accessible from various client devices through a thin client interface such as a web browser, e.g., web-based e-mail. The consumer does not manage or control the underlying cloud infrastructure including network, servers, operating systems, storage, or even individual application capabilities, apart from limited user-specific application configuration settings. Platform as a service provides the capability to the consumer to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations. Infrastructure as a service provides the capability to the consumer to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components, e.g., host firewalls.

The Deployment Models are private cloud, community cloud, public cloud and hybrid cloud. The private cloud infrastructure is operated solely for an organization. It may be managed by the organization or a third party and may exist on-premises or off-premises. The community cloud infrastructure is shared by several organizations and supports a specific community that has shared concerns, e.g., mission, security requirements, policy, and compliance considerations. It may be managed by the organizations or a third party and may exist on-premises or off-premises. The public cloud infrastructure is made available to the general public or a large industry group and is owned by an organization selling cloud services. The hybrid cloud infrastructure is a composition of two or more clouds (private, community, or public) that remain unique entities but are bound together by standardized or proprietary technology that enables data and application portability, e.g., cloud bursting for load-balancing between clouds.

Figure 6:
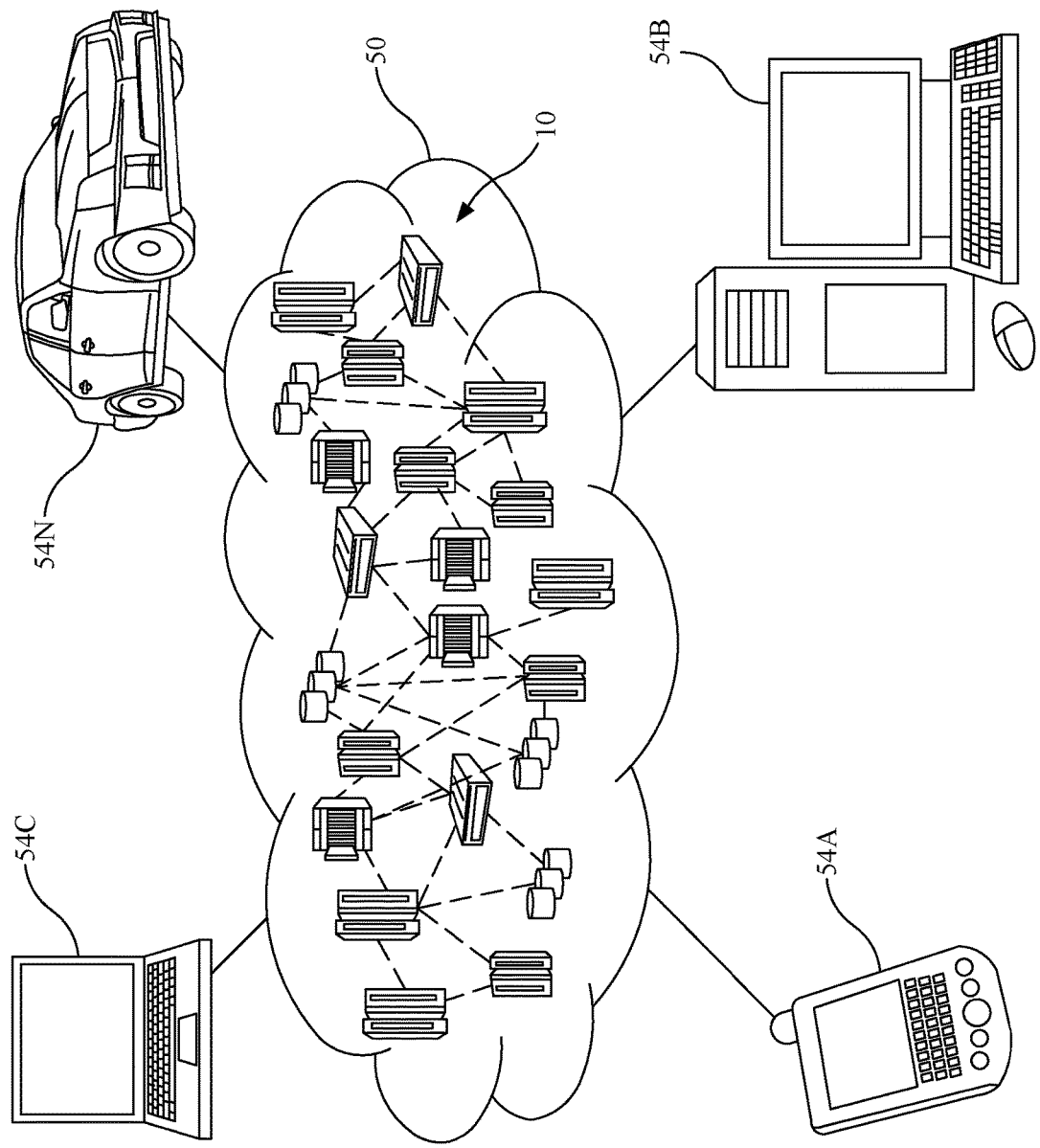
FIG. 6 depicts a cloud computing environment according to an embodiment of the present invention.

A cloud computing environment is service oriented with a focus on statelessness, low coupling, modularity, and semantic interoperability. At the heart of cloud computing is an infrastructure that includes a network of interconnected nodes. Referring now to FIG. 6, an illustrative cloud computing environment 50 is depicted. As shown, the cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection, e.g., using a web browser.

Figure 7:
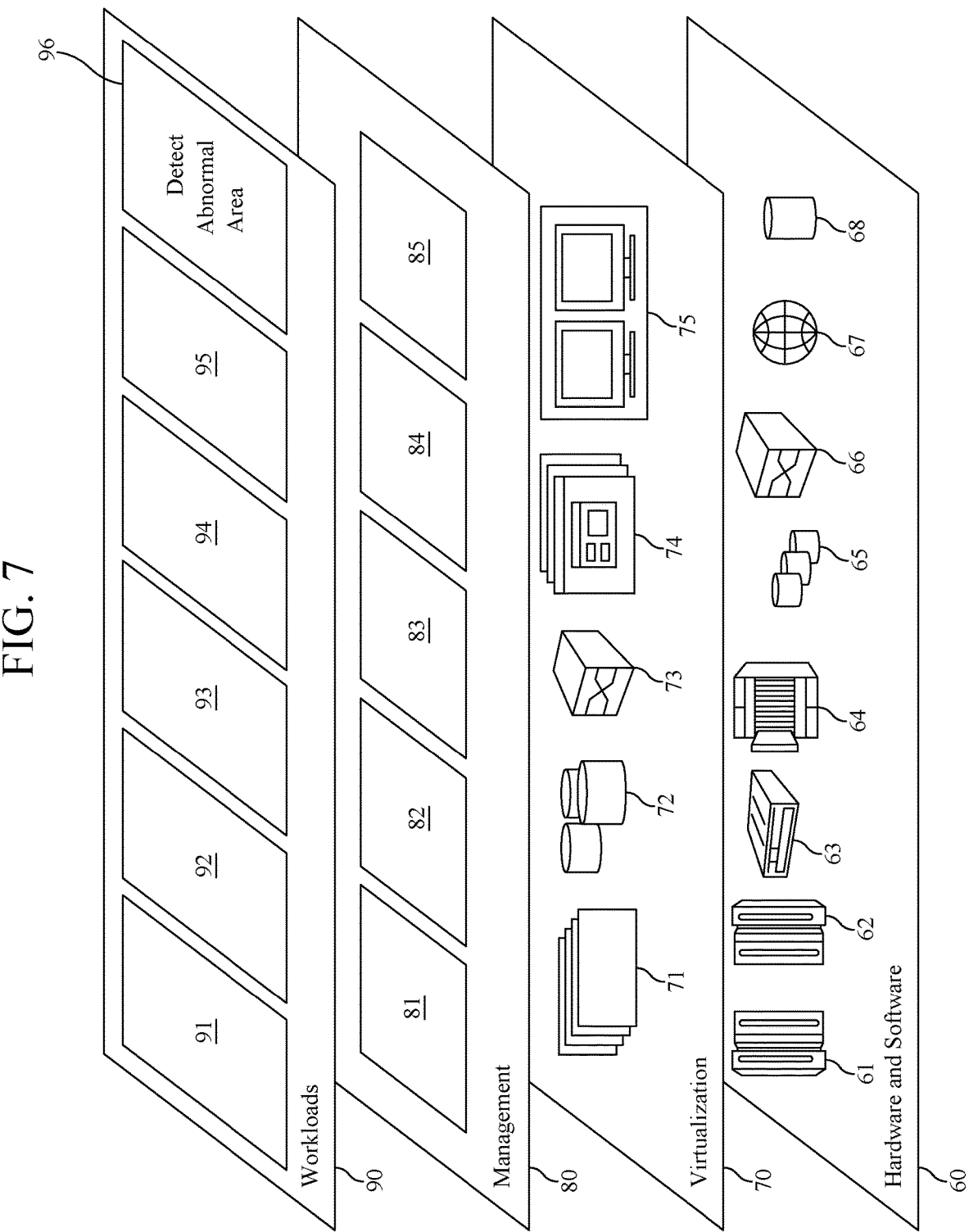
FIG. 7 depicts abstraction model layers according to an embodiment of the present invention.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided. A hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68. A virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and abnormal area detection 96.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s) and steps or elements from methods in accordance with the present invention can be executed or performed in any suitable order. Therefore, it will be understood that the appended claims are intended to cover all such modifications and embodiments, which would come within the spirit and scope of the present invention.

What is claimed is:

1. A method for identifying an abnormal area, the method comprising:
   identifying an initial spatial weights matrix between pairs of air quality sensors from a plurality of air quality sensors distributed across a geographical area, the spatial weights matrix utilizing a distance between each given pair of air quality sensors and wind direction through the geographical area;
   obtaining air quality data from each air quality sensor;

using the initial spatial weights matrix and air quality data to calculate a plurality of local moran's indexes, one for each air quality sensor;

using the plurality of local moran's indexes to divide the plurality of air quality sensors into four groups;

classifying each one of the four groups as a proper group or an improper group; and designating each group classified as a proper group for supervision as an abnormal area.

2. The method of claim 1, wherein identifying the initial spatial weights matrix comprises:

calculating a distance between each given pair of air quality sensors using location coordinates associated with each air quality sensor;

determining a node vector between each given pair of air quality sensors;

determining the wind direction; and setting a spatial weight between each given pair of air quality sensors based on a comparison between the wind direction and the node vector associated with the given pair.

3. The method of claim 2, wherein setting the spatial weight between each given pair of air quality sensors based on a comparison between the wind direction and the node vector further comprises:

defining the spatial weight between the given pair of air quality sensors as a cosine of an angle between the wind direction and the node vector divided by the distance between the given pair of air quality sensors when the given pair of air quality sensors has at least a node vector component extending in the wind direction; and defining the spatial weight between the given pair of air quality sensors as the negative of the cosine of the angle between the wind direction and the node vector divided by the distance between the given pair of air quality sensors when the given pair of air quality sensors lack at least a node vector component extending in the wind direction.

4. The method of claim 1, wherein the four groups comprise a statistically significant cluster group of high air quality values, a statistically significant cluster group of low air quality values, a high value outlier group comprising a high air quality value surrounded by low air quality values, and a low value outlier group comprising a low air quality value surrounded by high air quality values.

5. The method of claim 1, wherein classifying each one of the four groups comprises using a supervised classification model.

6. The method of claim 5, wherein the method further comprises building the supervised classification model by:

obtaining a plurality previously defined groups of air quality sensors, each previously defined group comprising air quality sensor locations, air quality data and a classification label, the classification label comprising proper or improper; and using each previously defined group to train the supervised classification model with features as model inputs and the classification label as a model output.

7. The method of claim 6, wherein the features comprise a largest inner group air quality data difference, a median inner group air quality difference, a largest whole group air quality data difference, and a geographical size.

8. The method of claim 1, wherein the method further comprises:

subdividing each group classified as an improper group into four sub-groups.

9. The method of claim 8, wherein subdividing each improper group comprises:

obtaining air quality data from each air quality sensor in each improper group;

using the initial spatial weights matrix and air quality data to calculate a plurality of local moran's indexes, one for each air quality sensor in each improper group;

using the plurality of local moran's indexes to divide the plurality of air quality sensors in each improper group into four sub-groups; and classifying each one of the four sub-groups from each improper group as either a proper sub-group or an improper sub-group using the supervised classification model.

10. The method of claim 9, wherein the four sub-groups comprise a statistically significant cluster of high air quality values, a statistically significant cluster of low air quality values, a high value outlier comprising a high air quality value surrounded by low air quality values, and a low value outlier comprising a low air quality value surrounded by high air quality values.

11. A computer-readable medium containing a computer-readable code that when read by a computer causes the computer to perform a method for identifying an abnormal area, the method comprising:

identifying an initial spatial weights matrix between pairs of air quality sensors from a plurality of air quality sensors distributed across a geographical area, the spatial weights matrix utilizing a distance between each given pair of air quality sensors and wind direction through the geographical area;

obtaining air quality data from each air quality sensor;

using the initial spatial weights matrix and air quality data to calculate a plurality of local moran's indexes, one for each air quality sensor;

using the plurality of local moran's indexes to divide the plurality of air quality sensors into four groups;

classifying each one of the four groups as a proper group or an improper group; and designating each group classified as a proper group for supervision as an abnormal area.

12. The computer-readable medium of claim 11, wherein identifying the initial spatial weights matrix comprises:

calculating a distance between each given pair of air quality sensors using location coordinates associated with each air quality sensor;

determining a node vector between each given pair of air quality sensors;

determining the wind direction; and setting a spatial weight between each given pair of air quality sensors based on a comparison between the wind direction and the node vector associated with the given pair.

13. The computer-readable medium of claim 11, wherein setting the spatial weight between each given pair of air quality sensors based on a comparison between the wind direction and the node vector further comprises:

defining the spatial weight between the given pair of air quality sensors as a cosine of an angle between the wind direction and the node vector divided by the distance between the given pair of air quality sensors when the given pair of air quality sensors has at least a node vector component extending in the wind direction; and defining the spatial weight between the given pair of air quality sensors as the negative of the cosine of the angle between the wind direction and the node vector divided by the distance between the given pair of air quality sensors when the given pair of air quality sensors lack at least a node vector component extending in the wind direction.

14. The computer-readable medium of claim 11, wherein the four groups comprise a statistically significant cluster group of high air quality values, a statistically significant cluster group of low air quality values, a high value outlier group comprising a high air quality value surrounded by low air quality values, and a low value outlier group comprising a low air quality value surrounded by high air quality values.

15. The computer-readable medium of claim 11, wherein the method further comprises:
   building a supervised classification model by:
      obtaining a plurality previously defined groups of air quality sensors, each previously defined group comprising air quality sensor locations, air quality data and a classification label, the classification label comprising proper or improper; and
      using each previously defined group to train the supervised classification model with features as model inputs and the classification label as a model output,
   wherein classifying each one of the four groups as either a proper group or an improper group comprises using the supervised classification model.

16. The computer-readable medium of claim 15, wherein the method further comprises:
   subdividing each group classified as an improper group into four sub-groups.

17. The computer-readable medium of claim 16, wherein subdividing each improper group comprises:
   obtaining air quality data from each air quality sensor in each improper group;
   using the initial spatial weights matrix and air quality data to calculate a plurality of local moran's indexes, one for each air quality sensor in each improper group;
   using the plurality of local moran's indexes to divide the plurality of air quality sensors in each group into four sub-groups; and
   classifying each one of the four sub-groups from each group as either a proper sub-group or an improper sub-group using the supervised classification model;
   wherein the four groups comprise a statistically significant cluster of high air quality values, a statistically significant cluster of low air quality values, a high value outlier comprising a high air quality value surrounded by low air quality values, and a low value outlier comprising a low air quality value surrounded by high air quality values.

18. A system for identifying an abnormal area, the system comprising:
   a plurality of air quality sensors distributed across a geographical area;
   a data collection system in communication with the plurality of air quality sensors to obtain air quality data from each air quality sensor and wind direction data through the geographical area;
   a clustering module in communication with the data collection system to identify an initial spatial weights matrix between pairs of air quality sensors using a distance between each given pair of air quality sensors and wind direction, to calculate a plurality of local moran's indexes, one for each air quality sensor from the initial spatial weights matrix and air quality data and to divide the plurality of air quality sensors into four groups based on the plurality of local moran's indexes;
   a classification module in communication with the clustering module to classify each one of the four groups as either a proper group or an improper group using a supervised classification model; and
   an output module in communication with the classification module and the clustering module to output each group classified as a proper group for supervision as an abnormal area.

19. The system of claim 18, wherein:
   the output module designates each group classified as an improper group for further subdivision; and
   the clustering module subdivides each group classified as an improper group into four sub-groups and communication the four sub-groups to the classification module to classify each one of the four sub-groups from each improper group as either a proper sub-group or an improper sub-group using the supervised classification model.

* * * * *